US010416129B2

(12) United States Patent
Jones et al.

(10) Patent No.: US 10,416,129 B2
(45) Date of Patent: Sep. 17, 2019

(54) CATALYTIC REACTOR COUPLED WITH FLAME IONIZATION DETECTOR FOR LIQUID CHROMATOGRAPHY

(71) Applicant: Activated Research Company, LLC, Eden Prairie, MN (US)

(72) Inventors: Andrew Jones, Minneapolis, MN (US); Charles Spanjers, St. Louis Park, MN (US)

(73) Assignee: ACTIVATED RESEARCH COMPANY, LLC, Eden Prairie, MN (US)

( * ) Notice: Subject to any disclaimer, the term of this patent is extended or adjusted under 35 U.S.C. 154(b) by 100 days.

(21) Appl. No.: 15/356,110

(22) Filed: Nov. 18, 2016

(65) Prior Publication Data
US 2017/0146496 A1 May 25, 2017

Related U.S. Application Data

(60) Provisional application No. 62/258,052, filed on Nov. 20, 2015.

(51) Int. Cl.
*G01N 30/68* (2006.01)
*G01N 30/84* (2006.01)
G01N 30/32 (2006.01)
B01J 23/56 (2006.01)
B01J 23/00 (2006.01)
G01N 30/06 (2006.01)

(52) U.S. Cl.
CPC ............. *G01N 30/68* (2013.01); *G01N 30/84* (2013.01); *G01N 2030/067* (2013.01); *G01N 2030/8435* (2013.01)

(58) Field of Classification Search
CPC ... B01J 23/00; B01J 23/38; B01J 23/40; B01J 23/42; B01J 23/44; B01J 23/46; B01J 23/56; G01N 30/68; G01N 30/64; G01N 30/32; G01N 30/02; G01N 30/06; G01N 2030/68; G01N 2030/022; G01N 2030/067
USPC ........................................................ 436/161
See application file for complete search history.

(56) References Cited

U.S. PATENT DOCUMENTS

| 3,954,408 | A |   | 5/1976  | Dugger           |            |
|-----------|---|---|---------|------------------|------------|
| 4,162,235 | A | * | 7/1979  | Acres ............... | B01D 53/945 |
|           |   |   |         |                  | 423/213.5  |
| 4,357,420 | A |   | 11/1982 | Bostick et al.   |            |
| 4,448,691 | A |   | 5/1984  | Davis            |            |
| 4,717,675 | A |   | 1/1988  | Sievers et al.   |            |
| 4,726,930 | A |   | 2/1988  | Matsushita et al.|            |
| 4,806,485 | A |   | 2/1989  | Birks et al.     |            |
| 4,837,161 | A |   | 6/1989  | Stevens et al.   |            |
| 2009/0069594 | A1 |   | 3/2009  | Gong et al.      |            |
| 2015/0010445 | A1 |   | 1/2015  | Makatsoris et al.|            |
| 2015/0079691 | A1 |   | 3/2015  | Fogwill et al.   |            |

OTHER PUBLICATIONS

Park et al, The reaction mechanism of catalytic oxidation with hydrogen, peroxide and ozone in aqueous solution, Water Science & Technology • Feb. 2003, vol. 47, No. 1, pp. 179-184. (Year: 2003).*
International Search Report from corresponding Application No. PCT/US2016/062892 dated Feb. 9, 2017.
Extended European Search Report issued in related European Patent Application No. 16867276.4, dated Jul. 11, 2019.
Rolf Gloor et al.: "Universal Detector for Monitoring Organic Carbon in Liquid Chromatography", Analytical Chemistry, vol. 51, No. 6, May 1, 1979, pp. 645-647.
Takuro Watanabe et al.: "Development of a Precise Method for the Quantitative Analysis of Hydrocarbons Using Post-Column Reaction Capillary Gas Chromatography with Flame Ionization Detection", Chromatography, vol. 27, No. 2, Jan. 1, 2006, pp. 49-55.
Vandamme D. et al.: "A Universal Gradient Apparatus for Multiple Organic Solvents-II. Fractionation and Elution of Serum Lipids", Analytical Biochemistry, Elsevier, Amsterdam, NL, vol. 69, No. 1, Nov. 1, 1975, pp. 29-33.

* cited by examiner

*Primary Examiner* — Christine T Mui
(74) *Attorney, Agent, or Firm* — E. Joseph Gess; Melissa Hayworth

(57) ABSTRACT

Provided is a system comprising a device that performs one or more reactions to liquid or supercritical fluid chromatograph effluents and produces molecules that are subsequently detected by a suitable detector. This allows for one to practice a method for the detection and quantification of organic molecules from a liquid chromatograph for the purpose of increasing detection limits and allowing for the universal detection of organic molecules. The linear dynamic range and molecular response are greater than those previously available.

29 Claims, 4 Drawing Sheets

CATALYTIC REACTOR COUPLED WITH FLAME IONIZATION DETECTOR FOR LIQUID CHROMATOGRAPHY

CROSS REFERENCE TO RELATED APPLICATIONS

The present application claims priority to U.S. Provisional Application 62/258,052, filed Nov. 20, 2015, which is herein incorporated by reference in its entirety.

BACKGROUND

Liquid chromatography (LC), also termed high performance liquid chromatography (HPLC) or supercritical fluid chromatography (SFC), is a technique used for the separation and quantification of molecules in a liquid. An analyte is injected onto a column filled with separation media and detected post-separation using one or more detectors. Many different types of detectors exist that operate on a variety of detection principles including refractive index (RI), ultra-violet-visible light (UV-VIS), evaporative light-scattering (ELSD), and mass spectrometry (MS) detectors. No single detector is capable of detecting all organic molecules and many have major limitations that restrict their use to certain classes of compounds and/or concentration ranges. For example, UV-VIS detectors are sensitive to molecules that have chromophores and absorb light in certain wavelengths. RI detectors have low sensitivities and are only sensitive to compounds that have refractive indices different from that of the solvent. MS detectors are difficult to use for quantification because of the large effects of solvents and they are highly sensitive to buffers found in LC streams. For these reasons, a variety of detectors are typically employed for robust chemical analysis. A detector that is highly sensitive to a broad range of organic compounds would drastically simplify analysis and reduce the costs of multiple detector schemes.

The flame ionization detector (FID) is a highly sensitive technology capable of detecting the majority of carbon containing compounds with a large linear response. The FID is the most common detector for gas chromatography, but no commercial LC-FID technology exists today because of the difficulties of sample introduction of non-volatile species into the flame. In addition, the large amount of organic solvents in typical LC streams can saturate the FID and lead to low, or negligible, detection.

Several methods for the introduction of samples into FIDs are known and include designs whereby the column effluent is applied to a moving substrate and the mobile phase is evaporated. The analytes are then carried on the moving substrate into a heated zone and volatilized either by boiling, gas-phase oxidation or gas-phase cracking reactions. These designs have included moving belts (Privett, O. S.; Erdahl, W. L., Anal. Biochem. 1978, 84:449), wires (Lapidus, B. M.; Karmen, A., J. Chromatogr. Sci. 1972, 10:103-106), chains (Karmen, A., J. Sep. Sci. 1967, 2:387-397), and rotating discs (Dubsky, H., J. Chromatogr. 1972, 71:395-399; U.S. Pat. No. 3,788,479A). Two commercial versions, which are now discontinued due to issues with sensitivity and reliability, were sold by Pye Unicam Ltd and Tracor Instruments. In addition, several methods have been described for the injection of LC streams directly into the FID using direct column connections (Guillemin, C. L.; Millet, J. L.; Dubois, J., J. High Resolut. Chromatogr. 1981, 4:280; Miller, D. J.; Hawthorne, S. B., Anal. Chem. 1997, 69:623-627) and nebulizers (Young, E.; Smith, R. M.; Sharp, B. L.; Bone, J. R., J. Chrom. A, 2012, 1236:16-20; WO2002018939A2; U.S. Pat. No. 8,920,658B2; U.S. Pat. No. 8,695,813B2; EP2089128A4; EP2089128A1), but these methods are restricted to the small subset of LC users who do not use organic solvents for separation (i.e., super-heated water chromatography or SHWC), they often have low analyte transfer efficiencies and the large amount of water can cause flame instabilities. Improved methods for the introduction of LC effluents to the FID are continually sought.

SUMMARY

The present invention relates to a reactor/device that performs one or more catalytic reactions to liquid or supercritical fluid chromatography effluents. The reactions generally convert the organic compounds present in the effluent to molecules that are subsequently detectable by a suitable detector, such as a flame ionization detector. The present reactor and method allow for one to practice a method for the detection and quantification of organic molecules received from a liquid chromatograph for the purpose of increasing detection limits, and allowing for the universal detection of organic molecules. The linear dynamic range and molecular response are greater than those previously available.

In one embodiment, there is provided a device/reactor which performs one or more catalytic reactions on organic analytes fed from a liquid chromatograph. In one embodiment, the reaction is a catalytic oxidation conducted in the presence of an oxidant such as hydrogen peroxide. In another embodiment, the reaction is a catalytic reduction conducted in the presence of a reducing agent such as hydrogen. In another embodiment, both oxidation and reduction reactions are conducted within the device/reactor. In yet another embodiment, the reaction does not require the addition of an oxidant or reductant.

In another embodiment, a method comprising receiving and catalytically oxidizing the effluent from a liquid chromatograph is provided. The oxidation products can then be reduced, and reduction products can then be passed to a suitable detector such as a FID. In one embodiment, the oxidation is conducted using hydrogen peroxide as the oxidant. In another embodiment, the oxidation reaction yields carbon dioxide as a product, which is then reduced to form methane.

In one embodiment, provided is a system comprising a liquid chromatograph, the reactor device of the present invention, and a FID. The effluent from the liquid chromatograph is passed to the reactor device in which one or more catalytic reactions on the organic analytes in the effluent are conducted. The products from the reactions are then passed to the FID for detection.

DETAILED DESCRIPTION

The present invention is a device that catalytically converts the organic compounds present in the effluent of liquid chromatography (including but not limited to supercritical liquid phases) columns into carbon dioxide, carbon monoxide, methane, water and other non-carbonaceous by-products for the subsequent introduction into a detector such as a FID. The device is a reactor with small internal channels containing catalyst particles, and is designed to minimize axial dispersion and back-mixing thereby reducing peak broadening effects. It has been found that this device, or a collection of such devices, enable(s) the quantitative transfer of carbon from liquid chromatograph streams to the FID, allowing for unprecedented sensitivity and versatile detection of many carbon compounds. The fixed reactor eliminates the reliability issues and transfer inefficiencies of moving parts (e.g., chains, wires and disks). Multiple device arrangements allow for solvent removal and the use of organic solvents. High transfer efficiencies and high sensitivities are found with the device.

In one embodiment, the effluent of an LC column is mixed with hydrogen peroxide and fed into a heated metal channel containing catalysts to oxidize carbon species to carbon dioxide. The effluent of this reaction is mixed with hydrogen and fed to another heated metal channel containing catalysts to reduce the carbon dioxide to methane. The mixture is optionally treated to remove water and fed to an FID.

In another embodiment the oxidant used is air. In other embodiments the oxidant is oxygen between 1-100% composition, ozone, perchlorate, nitric acid, or sulfuric acid.

In some embodiments the metal channels are manufactured using 3D printing. In other embodiments the channels are tubes or other designs from traditional manufacturing or lithography.

In certain embodiments the catalysts are designed such that only specific molecules react.

In certain embodiments carbon monoxide and/or carbon dioxide are fed to a detector.

In some embodiments the effluent is treated by adsorbing specific molecules before, during or after reactions.

In some embodiments gases are selectively removed from inlet, outlet, or reaction streams.

Figure 1:
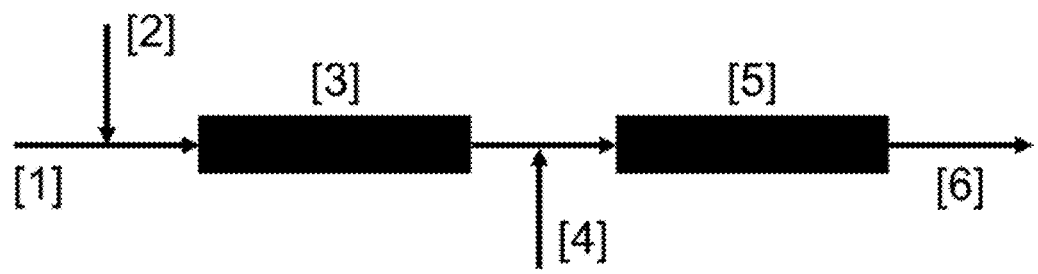
FIG. 1 shows one embodiment of the present invention involving oxidation and reduction reaction devices.

FIG. 1 shows one embodiment of the invention. In the embodiment, the device comprises an inlet [1] to an oxidation reaction device [3]. The inlet contains an effluent from a liquid chromatograph. The effluent from the liquid chromatograph in the inlet [1] (defined here as the "mobile phase") could be primarily water with intermittent concentrated or dilute analytes. Or the analytes could be dilute or concentrated and flowing continuously. The effluent in the inlet [1] could also be any organic solvent, including, for example, methanol, acetonitrile, or carbon dioxide. Other solvents used in liquid chromatography, with any amount of any other molecule, might also be in the effluent.

An oxidant is introduced into the inlet by a conduit [2]. The oxidant could be air, pure oxygen, hydrogen peroxide, perchlorate, ozone, nitric acid, sulfuric acid, or another oxidant. One purpose of adding an oxidant is to have enough oxygen to perform complete or partial oxidation (i.e., the complete conversion of organic analytes to $CO_2$ or partial oxidation of the analytes to CO). Another purpose of adding the oxidant may be to solvate the analytes in the liquid feed. Of particular advantage, hydrogen peroxide helps solvate and oxidize organic analytes such that they are not retained within the device. Without hydrogen peroxide, it was observed that molecules similar to glucose would be retained within the device, which is undesirable. The use of a solvating oxidant such as hydrogen peroxide also reduces the possibility of plugging within the system.

The oxidation reaction device [3] comprises an oxidation catalyst. Examples of suitable catalysts include catalysts comprising Ru, Ni, Pd, Pt, Co, Rh, Fe, Ir, Cu, or combinations thereof of these elements. In one embodiment, the catalyst is Pt. The purpose of a catalyst is to speed up the oxidation reaction to ensure complete combustion of organic analytes to $CO_2$, or partial combustion to CO.

The oxidation reaction could occur in channels packed with the aforementioned catalysts. The channels could have an internal diameter of any size, but preferably between 0.01 cm and 1.3 cm. The total volume of the internal channels could be smaller than 0.05 $cm^3$ or larger than 4 $cm^3$, but preferably between 0.05 $cm^3$ and 4 $cm^3$. The channels are small in diameter and volume to minimize peak broadening in order to retain good chromatography. The support for the oxidation catalyst could be titania, alumina, silica, or silica-alumina, but most preferably it is a non-porous silica support with particle sizes of approximately 0.25 mm. The outlet of the oxidation reaction device generally contains $CO_2$ and/or CO that is produced from the oxidation of analytes. Ideally, every organic compound that enters the oxidation reaction device is fully (>99%) converted to $CO_2$ and/or CO.

The reductant input [4] is preferably hydrogen gas, although other reducing agents can be used. The flow rate for hydrogen gas could be less than 5 $cm^3$ $min^{-1}$ or greater than 100 $cm^3$ $min^{-1}$, but preferably between 5 $cm^3$ $min^{-1}$ and 100 $cm^3$ $min^{-1}$, and ideally 40 $cm^3$ $min^{-1}$. The reduction reaction device [5] generally comprises a reduction catalyst which could include (but not limited to) Ru, Ni, Pd, Pt, Co, Rh, or Fe reduction catalysts, or combinations thereof of these elements. In one embodiment, the reduction catalyst is Ru. Ru possesses the highest hydrogenolysis turn-over rates, or the C—O bond breaking reaction rate that is necessary to produce methane. Methane is desired because it can be transported to and subsequently detected by a flame ionization detector (FID) with high sensitivity. Ideally, near full conversion (>99%) to methane of all CO and $CO_2$ entering the reduction reaction device is achieved. Full conversion of all organic analytes entering from the liquid chromatograph effluent to methane at the exit of the device [6] is desired.

The channels of the reduction reaction device could have internal diameters of any size, but preferably between 0.01 cm and 1.3 cm. The total volume of the internal channels could be smaller than 0.05 $cm^3$ or larger than 4 $cm^3$, but preferably between 0.05 $cm^3$ and 4 $cm^3$. The channels are small in diameter and volume to minimize peak broadening in order to retain good chromatography.

The exit stream generally containing methane [6] could be sent to an FID for detection of methane, because FIDs are highly sensitive and linear in response over seven orders of magnitude in methane concentration. Or, instead, the exit stream could be sent to another detector that is sufficiently sensitive for methane, or another by-product of the reaction. The benefits of this device combined with an FID over other devices used for detection of analytes in liquid chromatography include its ability to universally detect any organic analyte, its high sensitivity, and its linearity over seven orders of magnitude in analyte concentration.

Figure 2:
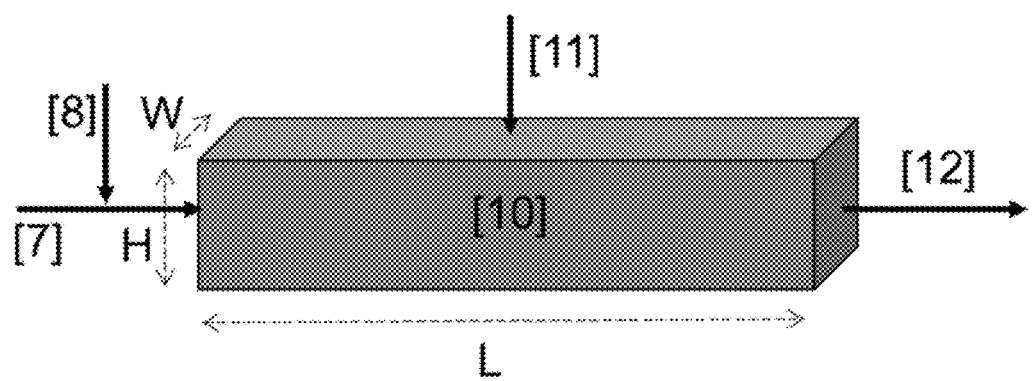
FIG. 2 shows a diagram of one embodiment of the present invention illustrating physical dimensions.

FIG. 2 shows a 3D view of the body [10] of one embodiment of the invention. The length of the device could be 1-3 in. (2.5-7.6 cm), the width could be 0.2-2 in (1.25-5 cm), and the height could be 0.1-1 in. (0.25-2.5 cm). The ideal size for one embodiment of the device is 2 in.×1 in.×0.5 in. (5 cm×2.5 cm×1.25 cm), as shown in FIG. 2. Stainless steel tubes are welded to the reactor to provide conduits for the gas flows. The conduit tubes that could be present are a liquid chromatograph effluent [7], an oxidant input [8], a reductant input [11], and an outlet [12]. The conduit tubes and/or the reactor can be coated with a silicon coating to prevent molecules from sticking or reacting on the inside of the tubes. Catalyst particles are retained within the device because of the geometries of the internal channels. The catalysts within the device could contain one or more of the following elements: Ni, Pt, Pd, Fe, Ru, Co, Cu and/or Rh. The catalyst supports may include powders of titania, alumina, silica-alumina, silica, or fibers thereof. The device is contained entirely within a solid stainless steel block, or any other suitable material such as Inconel, hastelloy, titanium etc., that is heated with a resistive heater to 200-800° C. In one embodiment, the temperature is in the range of from 300-500° C. The temperature can be measured with a thermocouple or resistive temperature detector (RTD).

Figure 3:
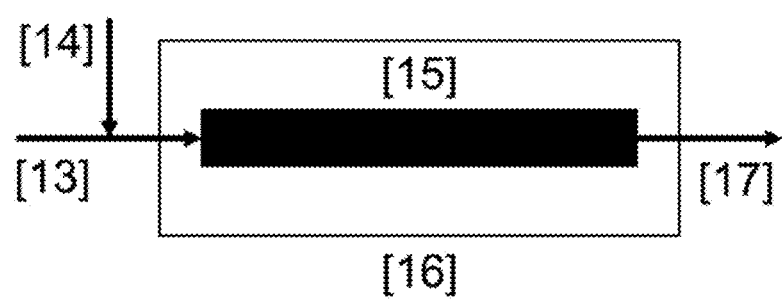
FIG. 3 shows one embodiment of the present invention comprising an oxidation reaction device.

FIG. 3 shows another embodiment of the invention. In this embodiment, the device comprises an inlet [13] containing effluent from a liquid chromatograph, an oxidant input [14], a reactor body [16], an oxidation reaction device [15], and an outlet [17]. The inlet containing effluent from the liquid chromatograph [13] could be primarily water with intermittent concentrated or dilute analytes. Or the analytes could be dilute or concentrated and flowing continuously. The inlet could also be any other solvent including methanol, acetonitrile, carbon dioxide, or another solvent that is used commonly in liquid chromatography with any amount of any other molecule. In particular, this device could be used in conjunction with supercritical fluid chromatography (SFC) where $CO_2$ is the mobile phase and methanol is used as a modifier to help analytes separate and elute. Or the device could be used in conjunction with systems that have water and methanol in the mobile phase. The oxidant [14] could be air, pure oxygen, hydrogen peroxide, perchlorate, ozone, or another oxidant. One purpose of adding an oxidant is to have enough oxygen to perform complete or partial oxidation (i.e., the complete conversion of organic analytes to $CO_2$ or partial oxidation of the analytes to CO). Another purpose of adding the oxidant may be to solvate the analytes in the liquid feed [13]. For example, hydrogen peroxide helps solvate and oxidize organic analytes such that they are not retained within the device. Without hydrogen peroxide, it was observed that molecules similar to glucose would be retained within the device, which is undesirable.

The oxidation reaction device [15] comprises an oxidation catalyst which is generally comprised of Ru, Ni, Pd, Pt, Co, Rh, Fe, Ir, Cu, or combinations thereof of these elements. Most preferably the catalyst is Pt. The purpose of a catalyst is to speed up the oxidation reaction to ensure complete combustion of organic analytes to $CO_2$, or partial combustion to CO. The oxidation reaction could occur in channels packed with the aforementioned catalysts. The channels could have an internal diameter of any size, but preferably between 0.01 cm and 1.3 cm. The total volume of the internal channels could be smaller than 0.05 $cm^3$ or larger than 4 $cm^3$, but preferably between 0.05 $cm^3$ and 4 $cm^3$. The channels are small in diameter and volume to minimize peak broadening in order to retain good chromatography. The support for the oxidation catalyst could be titania, alumina, silica, or silica-alumina, but most preferably it is non-porous silica support with particle sizes of approximately 0.25 mm.

The outlet of the oxidation reaction device [17] generally contains $CO_2$ and/or CO produced from the oxidation of the mobile phase and/or analytes. It can be advantageous if the system does not convert all analytes to CO or $CO_2$. In this scenario, the mobile phase could contain methanol that is converted to CO, whereas analytes are not converted to CO. The advantage of such a device is that the baseline signal from methanol in the mobile phase would be reduced when using an FID detector because an FID does not detect CO. Then, the analytes could be analyzed by the FID because they are not completely converted to CO and still contain CH moieties that are detectable by FID. Alternatively, all of the analytes could be converted to CO or $CO_2$ and be detected by a device other than an FID such as an infrared sensor, a mass spectrometer, or another detector sufficiently sensitive to CO or $CO_2$.

Figure 4:
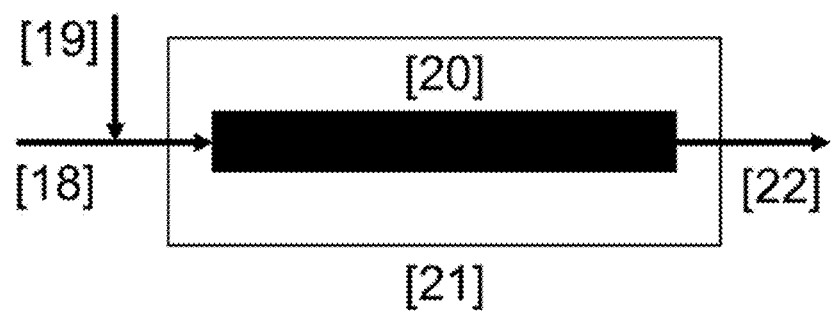
FIG. 4 shows one embodiment of the present invention comprising a reduction reaction device.

FIG. 4 shows another embodiment of the invention. In this embodiment, the device comprises an inlet [18] containing effluent from a liquid chromatograph, a reductant input [19], a reactor body [21], a reduction reaction device [20], and an outlet [22]. The inlet containing effluent from the liquid chromatograph [18] could be primarily water with intermittent concentrated or dilute analytes. Or the analytes could be dilute or concentrated and flowing continuously. The inlet could also be any other solvent including methanol, acetonitrile, carbon dioxide, or other solvent that is used commonly in liquid chromatography, with any amount of other molecules. The reduction reaction device [20] comprises a reduction catalyst. The catalyst in one embodiment comprises a reduction catalyst comprised of Ru, Ni, Pd, Pt, Co, Rh, or Fe reduction catalysts, or combinations of these elements. The most preferable reduction catalyst is Ru because Ru possesses the highest ability of these elements to perform hydrogenolysis, the C—O bond breaking reaction that is necessary to produce methane, $CH_4$. Methane is desired because it can be detected by a flame ionization detector (FID). Ideally, near full conversion (>99%) to methane of all CO and $CO_2$ entering the reduction reaction device is achieved. Full conversion of all organic analytes entering from the liquid chromatograph effluent [18] to methane at the exit of the device [22] is desired.

The channels of the reduction reaction device could have internal diameters of any size, but preferably between 0.01 cm and 1.3 cm. The total volume of the internal channels could be smaller than 0.05 $cm^3$ or larger than 4 $cm^3$, but preferably between 0.05 $cm^3$ and 4 $cm^3$. The channels are small in diameter and volume to minimize peak broadening in order to retain good chromatography. The exit stream containing methane [6] could be sent to an FID for detection of methane, because FIDs are highly sensitive and linear in response over seven orders of magnitude in methane concentration. Or, instead, the exit stream could be sent to another detector that is sufficiently sensitive for methane, or another by-product of the reaction.

Figure 5:
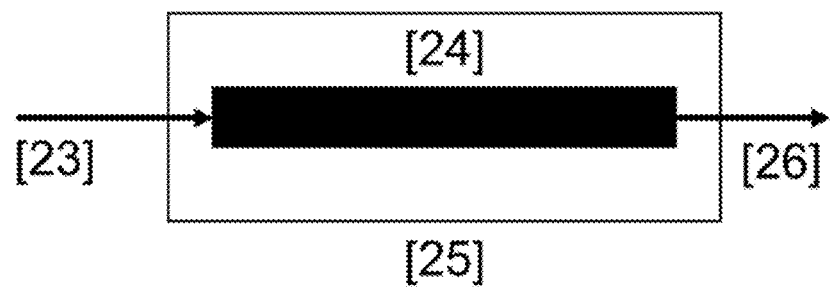
FIG. 5 shows one embodiment of the present invention comprising a reaction device.

FIG. 5 shows another embodiment of the invention. In this embodiment, the device comprises an inlet [23] containing effluent from a liquid chromatograph, a reaction device [24], a reactor body [25], and an outlet from the device [26]. Different from the above embodiments, this embodiment does not include an oxidant or reductant input. The liquid chromatograph effluent that pertains most to this device is a stream of $CO_2$ and methanol, but could refer to other liquid streams. Such a composition can be found for devices that perform supercritical fluid chromatography. When supercritical fluid chromatography is paired with an FID in the traditional manner, the system can only be used when there is no organic modifier (e.g., methanol) in the mobile phase because the FID will be saturated by the signal from methanol. Therefore, the methanol must be removed or selectively converted to a molecule that has no response in an FID. In this embodiment, the reaction device [24] performs selective conversion of methanol to CO. The reaction can be described as methanol decomposition and the reaction scheme is as follows: $CH_3OH \rightarrow CO+2H_2$. The catalysts and conditions are selected to minimize or prevent the decomposition of other molecules. For example, the molecular formula of ibuprofen (isobutylphenylpropanoic acid) is $C_{13}H_{18}O_2$. The maximum number of CO molecules that could be produced from this molecule is 2. After the reaction, at least 11 carbon atoms with CH moieties would remain and produce a signal in the FID detector.

The reaction device [24] comprises a catalyst which could include (but not limited to) Cu, Ru, Ni, Pd, Pt, Co, Rh, or Fe reduction catalysts, or combinations of these elements. The most preferable catalyst for the reaction is Cu because it is most active for this reaction and limits side products. The channels of the reaction device could have internal diameters of any size, but preferably between 0.01 cm and 1.3 cm. The total volume of the internal channels could be smaller than 0.05 $cm^3$ or larger than 4 $cm^3$, but preferably between 0.05 $cm^3$ and 4 $cm^3$. The channels are small in diameter and volume to minimize peak broadening in order to retain good chromatography. The exit stream containing non-oxidized molecules [26] could be sent to an FID for detection of organic molecules, because FIDs are highly sensitive and linear in response over many orders of magnitude in analyte concentration. Or, instead, the exit stream could be sent to another detector that is sufficiently sensitive for organic molecules or reaction byproducts.

Figure 6:
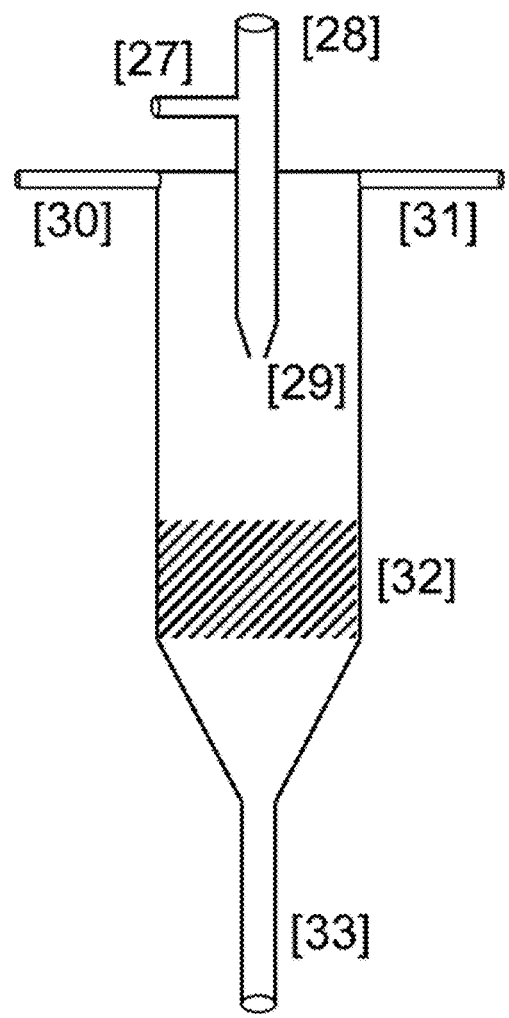
FIG. 6 shows a diagram of one embodiment of the present invention comprising a nozzle and oxidation reaction device.

FIG. 6 shows one embodiment of a specific design of an oxidation reaction device. This device comprises an inlet [28] containing effluent from a liquid chromatograph, an oxidant inlet [27], a nozzle for spraying the liquid and/or gas [29], an additional carrier gas or oxidant inlet [30], a vent outlet [31], an oxidation catalyst [32], and an outlet [33]. The liquid chromatograph effluent [28] could be any of those previously described herein. The oxidant inlet [27] could contain any oxidant molecule described herein. The nozzle could be a constriction of the inlet tube [28] that assists in creating liquid droplets that contact the catalyst bed [32]. The additional carrier gas or oxidant inlet [30] could be used for an inert carrier gas such as helium, argon, nitrogen, or the like. Or, it could be used for an oxidant. The vent outlet [31] is used to control the ratio of the inlet stream that is split to the vent or split to the outlet of the device [33], and could also be placed near the outlet of the device [33]. The catalyst [32] could consist of any oxidation catalyst that has been mentioned herein. The benefit of this oxidation reaction device over other designs is that it allows for the liquid to make direct contact with a hot catalyst. A simple tube, for example, would potentially lead to fouling from analytes sticking on the inner walls. Because this design allows for direct contact of the liquid with a hot catalyst while maintaining a lower temperature of the inlet tube [29], fouling would be minimized.

Figure 7:
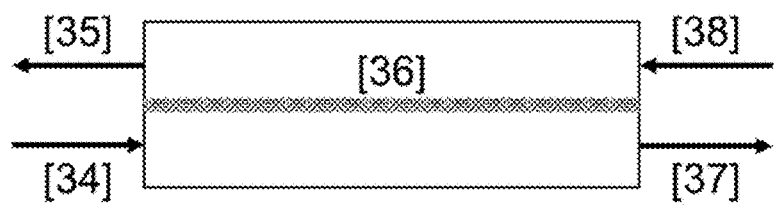
FIG. 7 shows one embodiment of the present invention comprising a semi-permeable membrane device for separation.

FIG. 7 shows one embodiment of a separation device that could be used in conjunction with any of the aforementioned devices. The device comprises an inlet from a liquid chromatograph or reactor effluent [34], an outlet [37], a semipermeable membrane [36], a fluid inlet [38], and a fluid outlet [35]. The purpose of this device is to remove methanol, acetonitrile, $CO_2$, CO, $H_2O$ and other small molecules from a liquid chromatograph effluent stream prior to reaction and detection. As small molecules from the effluent [34] travel past the membrane [36], they will diffuse from a high concentration to a lower concentration in the fluid [38]. The extract fluid [35] has a lower concentration of the target molecule to remove (e.g., methanol and acetonitrile) than the liquid chromatograph effluent. Increased pressure could instead be used to create the driving force for molecular motion through the membrane. The counter-current design is the preferred design because of its improved separation capacity compared to co-current flow, for example. The semipermeable membrane is optimally one that will allow the targeted molecule to diffuse through, but block the analytes of interest to diffuse through. Such membranes may be those typically designed for reverse osmosis or nanofiltration applications and have pore sizes in the range of 1 to 20 Å. Examples of companies that build these membranes are Evonik, Applied Membranes Inc., Dow Chemical/The FilmTec Corp., and GE Osmonics. The membrane may be a film, hollow-fiber, or other geometry. Ideally, this device reduces the concentration of methanol and acetonitrile to zero or below 1 ppm in the outlet [37]. The advantage of such a device is that the baseline signal obtained from solvents in an FID or another detector could be reduced or eliminated. Lower baseline signals lead to enhanced detection limits and ultimately superior chromatographic results. The extractant fluid could be pure water, a mixture of water and hydrogen peroxide, or another liquid, gas, liquid mixture, or a gas mixture. Hydrogen peroxide is desirable because it helps to solvate organic molecules and prevent fouling.

Figure 8:
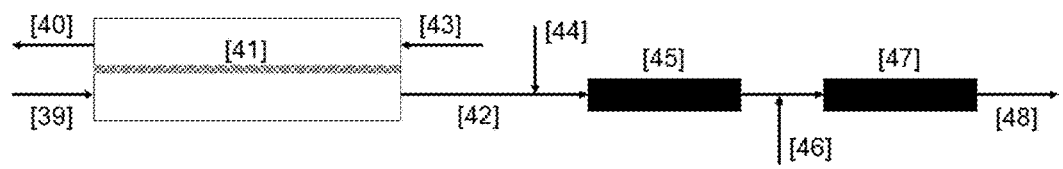
FIG. 8 shows one embodiment of the present invention comprising a system which performs separation, oxidation, and reduction.

FIG. 8 shows one embodiment of a system comprising a liquid chromatograph effluent inlet [39], a fluid outlet [40], a semipermeable membrane [41], an outlet of the separation device [42], a fluid inlet [43], an oxidant inlet [44], an oxidation reaction device [45], a reductant inlet [46], a reduction reaction device [47], and an outlet [48]. Such a device could remove the organic solvents from a liquid chromatograph effluent, oxidize organic analytes to CO or $CO_2$, and subsequently reduce CO and $CO_2$ (that originated from organic analytes) to $CH_4$. Ultimately this system allows for highly-sensitivity detection of most organic analytes originating from a liquid chromatograph system when paired with an FID or another detector sufficiently sensitive for detecting methane or reaction by-products such as $N_2$, halogens, and sulfur.

Figure 9:
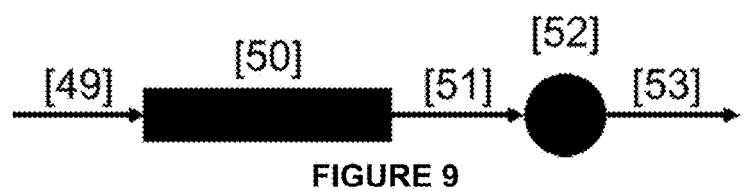
FIG. 9 shows one embodiment of the present invention comprising a system which performs a catalytic reaction and a flame ionization detector.

FIG. 9 shows one embodiment of a system comprising an inlet from a liquid chromatograph [49], a device that performs one or more catalytic reaction(s) on organic analytes [50], an outlet of the reaction device [51], an FID detector [52], and an outlet of the FID detector [53]. This system is superior to other liquid chromatograph detection systems because it is universally-sensitive to organic analytes.

Three-dimensional metal printing, or additive manufacturing, can be used to construct any or all of the aforementioned devices. This technology allows for precise control of internal geometries. The small, complex, geometries that are required in one embodiment of the invention could not be created by alternative reactor construction methods, such as machining. The selective laser sintering systems used for three-dimensional printing are available commercially. One such company that sells selective laser printers is 3D systems. The reactor body that is described in one embodiment is constructed by the printer layer-by-layer, which produces the complex internals. After, or during the printing process, the catalyst is packed into the reactor using mechanical force or injected as a slurry. The small size of the device allows for easy placement and integration within existing chromatograph hardware, and increases the thermal response of the device. A uniform temperature distribution of the device is obtained as a result of the seamless construction. The internal volume and geometries of the device are selected to eliminate dead volume and axial dispersion to ensure minimal additions to the axial dispersion already present in the chromatograph separation.

This reaction system paired with a detector such as the FID improves upon the analytical range, sensitivity and robustness of typical LC detectors. Furthermore, the small form factor of the device allows for easy placement within existing LC equipment without modification. The simplicity of the device allows for the system to be sold at prices comparable to, or cheaper than, alternative detectors for LC systems. The enclosed device ensures that catalysts which contain known health hazards are not unintentionally exposed to the environment or users.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention.

What is claimed is:

1. A system comprising:
    a liquid or supercritical fluid chromatograph;
    a reactor;
    a conduit connecting a chromatograph outlet with an inlet of the reactor whereby effluent containing organic analytes from the chromatograph is passed to the reactor; and
    the reactor is constructed to perform a catalytic oxidation reaction on organic analytes received from the chromatograph to thereby produce CO or $CO_2$ over a catalyst comprising Ru, Ni, Pd, Pt, Co, Rh, Fe, Ir, or Cu.

2. The system of claim 1, further comprising a conduit for introducing an oxidant into the reactor for use in the oxidation reaction.

3. The system of claim 2, wherein the oxidant is air, hydrogen peroxide, perchlorate, ozone, oxygen, nitric acid, or sulfuric acid.

4. The system of claim 3, wherein the oxidant comprises hydrogen peroxide.

5. The system of claim 2, wherein a catalyst comprised of one or more of Ru, Ni, Pd, Pt, Co, Rh, Fe, Ir, or Cu is used in the oxidation reaction.

6. The system of claim 5, wherein the catalysts are supported on titania, alumina, silica, or silica-alumina.

7. The system of claim 1, wherein the reactor has internal channels with internal diameters of 0.01 cm to 1.3 cm.

8. The system of claim 7, wherein the internal channels of the reactor has a total volume between 0.05 $cm^3$ and 4 $cm^3$.

9. The system of claim 2, further comprising a conduit from the reactor to a reduction reactor whereby product obtained from the oxidation is passed to a reduction reactor.

10. The system of claim 9, wherein the reduction reactor comprises a catalyst comprised of Ru, Ni, Pd, Pt, Co, Rh, and/or Fe reduction catalysts, or combinations thereof.

11. The system of claim 9, wherein the catalysts in at least one of the reactors are supported on an amorphous silica support.

12. The system of claim 1, wherein the reactor has a width of 0.5-2 in (1.25-5 cm), a length of 1-3 in. (2.5-7.6 cm), and a height of 0.1-1 in (0.25-2.5 cm).

13. The system of claim 1, wherein the reactor is heated to 200-800° C.

14. The system of claim 1, wherein three-dimensional printing, or additive manufacturing, was used to construct the reactor.

15. A method comprising
    (i) receiving effluent from a liquid or supercritical fluid chromatograph to a reactor, and
    (ii) oxidizing organic analytes in the effluent to CO or $CO_2$ in the reactor over a catalyst comprising Ru, Ni, Pd, Pt, Co, Rh, Fe, Ir, or Cu.

16. The method of claim 15, wherein hydrogen peroxide is used to oxidize the effluent.

17. The method of claim 16, wherein carbon monoxide and/or carbon dioxide is obtained from the oxidation and is subsequently reduced to form methane.

18. The method of claim 17, wherein the carbon monoxide and/or carbon dioxide is reduced over a catalyst comprised of Ru, Ni, Pd, Pt, Co, Rh, and/or Fe.

19. The method of claim 17, further comprising passing methane to a flame ionization detector.

20. The method of claim 17, wherein hydrogen is used in the reduction.

21. The method of claim 15, wherein methanol is decomposed to form one molecule of carbon monoxide and two molecules of hydrogen.

22. The method of claim 15, wherein a nebulizer is used to spray a condensed phase onto the oxidation catalyst.

23. The method of claim 15, wherein a semi-permeable membrane is used to remove select molecules from the liquid chromatograph effluent prior to reaction.

24. The method of claim 23, wherein methanol is removed from the liquid chromatograph effluent.

25. The method of claim 23, wherein acetonitrile is removed from the liquid chromatograph effluent.

26. The method of claim 16, wherein the oxidation products are fed to a flame ionization detector.

27. The method of claim 15, wherein the CO or $CO_2$ is passed to a detector.

28. A system for the detection and quantification of organic molecules from a liquid chromatograph comprising:
    a liquid or supercritical fluid chromatograph having an outlet;
    a device which contains a semi-permeable membrane that removes methanol and/or acetonitrile from the chromatograph effluent, the device having an inlet and an outlet;
    a conduit connecting the outlet of the chromatograph with the inlet of the device for removing methanol and/or acetonitrile;
    an oxidation reaction device with an inlet and an outlet, and containing a catalyst comprising Ru, Ni, Pd, Pt, Co, Rh, Fe, Ir, or Cu;

a conduit connecting the outlet of the device for removing methanol and/or acetonitrile with the inlet of the oxidation reaction device;

a reduction reaction device having an inlet and an outlet; and a conduit connecting the outlet of the oxidation reaction device with the inlet of the reduction reaction device.

29. The system of claim 28, wherein a flame ionization detector is utilized at the output of the reduction reaction device, and the outlet of the reduction reaction device is connected to an inlet of the flame ionization detector by a conduit.

* * * * *